(12) United States Patent
Tolleson et al.

(10) Patent No.: US 6,846,960 B2
(45) Date of Patent: Jan. 25, 2005

(54) PROCESS FOR REDUCING FLUORIDE IMPURITIES RESULTING FROM USE OF FLUOROPHOSPHITE CATALYSTS

(75) Inventors: Ginette Struck Tolleson, Longview, TX (US); Thomas Allen Puckette, Longview, TX (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/244,264

(22) Filed: Sep. 16, 2002

(65) Prior Publication Data

US 2004/0059161 A1 Mar. 25, 2004

(51) Int. Cl.[7] .............................................. C07C 45/00
(52) U.S. Cl. ...................................... 568/429; 568/454
(58) Field of Search .................................. 568/429, 454

(56) References Cited

U.S. PATENT DOCUMENTS

| | | | |
|---|---|---|---|
| 3,239,566 A | | 3/1966 | Slaugh et al. |
| 3,284,350 A | * | 11/1966 | Williamson |
| 3,527,809 A | | 9/1970 | Pruett et al. |
| 3,959,132 A | * | 5/1976 | Singh |
| 4,608,239 A | | 8/1986 | Devon |
| 4,789,753 A | | 12/1988 | Billig et al. |
| 4,912,155 A | | 3/1990 | Burton |
| 5,208,362 A | | 5/1993 | Glass et al. |
| 5,840,647 A | | 11/1998 | Puckette et al. |

FOREIGN PATENT DOCUMENTS

| | | |
|---|---|---|
| WO | WO 02 098825 A | 12/2002 |
| WO | WO 03 061822 A | 7/2003 |

OTHER PUBLICATIONS

Lewis, Richard J. Hawley's Condensed Chemical Dictionary, 13th Ed. p. 21.*
U.S. patent application Ser. No. 10/244,297, Tolleson et al., filed Sep. 16, 2002.
G. J. Klender, Adv. In Chem. Series, No. 249 "Polymer Durability", Ed. R. L. Clough, Am. Chem. Soc., p. 407–410.
Riesel et al., J.Z. Anorg. Allg. Chem. (1991), pp. 145–150, vol. 603.
Tullock et al., J. Org. Chem. (1960), pp. 2016–2019, vol. 25.
White et al., J. Am. Chem. Soc. (1970), pp. 7125–7135, vol. 92.
Meyer et al., Z. Naturforsch, Bi. Chem. Sci. (1993) pp. 659–671, vol. 48.
Written Opinion from the European Patent Office dated Apr. 30, 2004.

* cited by examiner

*Primary Examiner*—Shailendra Kumar
*Assistant Examiner*—Sikarl A. Witherspoon
(74) *Attorney, Agent, or Firm*—Jonathan D. Wood; Bernard J. Graves, Jr.

(57) ABSTRACT

Disclosed is a process for reducing fluoride content in a process utilizing a fluorophosphite-containing transition metal catalyst.

16 Claims, No Drawings

PROCESS FOR REDUCING FLUORIDE IMPURITIES RESULTING FROM USE OF FLUOROPHOSPHITE CATALYSTS

FIELD OF THE INVENTION

This invention relates to a process for reducing the amount of fluoride present in a process that utilizes a fluorophosphite-containing transition metal catalyst. More particularly, this invention relates to a process for producing products using a fluorophosphite-containing transition metal catalyst, wherein an additive is introduced into the reaction mixture of the process to reduce the amount of fluoride in the product.

BACKGROUND OF THE INVENTION

It is known from U.S. Pat. No. 5,840,647 that certain fluorophosphite ligands may be used to form transition metal complexes that serve as catalysts in a wide variety of transition metal catalyzed processes. A particularly suitable process is the hydroformylation or oxo reaction to form aldehydes. It is further known from the above patent that fluorophosphite diester compounds are useful as ligands in catalyst systems for the conversion of olefins to aldehydes. The fluorophosphite ligands can be substituted for, or used in combination with, known phosphite and/or phosphine ligands in a wide variety of catalyst systems using a transition metal as the primary catalyst component. Thus, the catalyst system comprises a combination of one or more transition metals selected from the Group VIII metals and rhenium and one or more fluorophosphite compounds having the general formula

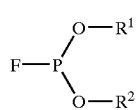

(I)

wherein $R^1$ and $R^2$ are hydrocarbyl radicals which contain a total of up to about 40 carbon atoms and wherein the ratio of gram moles fluorophosphite ligand to gram atoms transition metal is at least 1:1. The catalyst systems may be used in a wide variety of transition metal-catalyzed processes such as, for example, hydroformylation, hydrogenation, isomerization, hydrocyanation, hydrosilation, carbonylations, oxidations, acetoxylations, epoxidations, hydroamination, dihydroxylation, cyclopropanation, telomerizatons, carbon hydrogen bond activation, olefin metathesis, olefin dimerizations, oligomerizations, olefin polymerizations, olefin-carbon monoxide copolymerizations, butadiene dimerization and oligomerization, butadiene polymerization, and other carbon-carbon bond forming reactions such as the Heck reaction and arene coupling reactions. The catalyst systems comprising rhodium as the transition metal are especially useful for the hydroformylation of olefins to produce aldehydes and, therefore, are preferred.

When using the above fluorophosphite-containing transition metal catalysts in the various types of processes, there is a possibility that fluoride may be present in the processes due to decomposition of the fluorophosphite ligand transition metal complex. Therefore, when using a fluorophosphite-containing transition metal catalyst to produce a product, it would be desirable to have a means for reducing the amount of fluoride which may be produced during production processes.

It is therefore an object of this invention to provide a process of using a fluorophosphite-containing transition metal catalyst wherein the amount of fluoride which may be produced in the process is reduced.

SUMMARY OF THE INVENTION

The present invention comprises the addition of an additive into the reaction mixture of a fluorophosphite-containing transition metal catalyzed process to reduce the amount of fluoride present in the process.

DETAILED DESCRIPTION OF THE INVENTION

The present invention comprises the addition of an additive into the reaction mixture of a fluorophosphite-containing transition metal catalyzed process to reduce the amount of fluoride present in the process. Reducing the fluoride concentration in a process decreases corrosion problems and decreases the amount of fluoride contained in the products of the process.

The process of the present invention is applicable to any transition metal-catalyzed process utilizing a fluorophosphite-containing catalyst. Examples of such processes are hydrogenation, isomerization, hydrocyanation, hydrosilation, carbonylations, oxidations, acetoxylations, epoxidations, hydroamination, dihydroxylation, cyclopropanation, telomerizatons, carbon hydrogen bond activation, olefin metathesis, olefin dimerizations, oligomerizations, olefin polymerizations, olefin-carbon monoxide copolymerizations, butadiene dimerization and oligomerization, butadiene polymerization, and other carbon-carbon bond forming reactions such as the Heck reaction and arene coupling reactions. Preferably the process is the hydroformylation or oxo reaction to form aldehydes. The catalyst systems comprising rhodium as the transition metal are especially useful for the hydroformylation of olefins to produce aldehydes and, therefore, are preferred.

The fluorophosphite-containing catalysts of the present invention are defined in U.S. Pat. No. 5,840,647. More particularly, the fluorophosphite-containing catalyst comprises a combination of one or more transition metals selected from the Group VIII metals and rhenium and one or more fluorophosphite compounds having the general formula

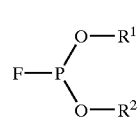

(I)

wherein $R^1$ and $R^2$ are hydrocarbyl radicals which contain a total of up to about 40 carbon atoms and wherein the ratio of gram moles fluorophosphite ligand to gram atoms transition metal is at least 1:1.

Fluorophosphite ester compounds having the formula

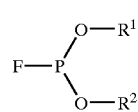

(I)

function as effective ligands when used in combination with transition metals to form catalyst systems for the processes described hereinabove. The hydrocarbyl groups represented by $R^1$ and $R^2$ may be the same or different, separate or combined, and are selected from unsubstituted and substituted alkyl, cycloalkyl and aryl groups containing a total of up to about 40 carbon atoms. The total carbon content of substituents $R^1$ and $R^2$ preferably is in the range of about 2 to 35 carbon atoms. Examples of the alkyl groups which $R^1$ and/or $R^2$ separately or individually can represent include ethyl, butyl, pentyl, hexyl, 2-ethylhexyl, octyl, decyl, dodecyl, octadecyl and various isomers thereof. The alkyl groups may be substituted, for example, with up to two substituents such as alkoxy, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts and the like. Cyclopentyl, cyclohexyl and cycloheptyl are examples of the cycloalkyl groups $R^1$ and/or $R^2$ individually can represent. The cycloalkyl groups may be substituted with alkyl or any of the substituents described with respect to the possible substituted alkyl groups. The alkyl and cycloalkyl groups which $R^1$ and/or $R^2$ individually can represent preferably are alkyl of up to about 8 carbon atoms, benzyl, cyclopentyl, cyclohexyl or cycloheptyl.

Examples of the aryl groups which $R^1$ and/or $R^2$ individually can represent include carbocyclic aryl such as phenyl, naphthyl, anthracenyl and substituted derivatives thereof. Examples of the carbocyclic aryl groups which $R^1$ and/or $R^2$ individually can represent the radicals having the formulas

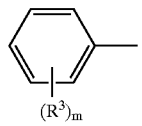

(II)

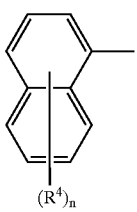

(III)

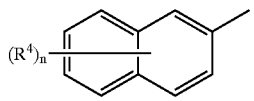

(IV)

wherein $R^3$ and $R^4$ may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts and the like. The alkyl moiety of the aforesaid alkyl, alkoxy, alkanoyl, alkoxycarbonyl and alkanoyloxy groups typically contains up to about 8 carbon atoms. Although it is possible for m to represent 0 to 5 and for n to represent 0 to 7, the value of each of m and n usually will not exceed 2. $R^3$ and $R^4$ preferably represent lower alkyl groups, i.e., straight-chain and branched-chain alkyl of up to about 4 carbon atoms, and m and n each represent 0, 1 or 2.

Alternatively, $R^1$ and $R^2$ in combination or collectively may represent a divalent hydrocarbylene group containing up to about 40 carbon atoms, preferably from about 12 to 36 carbon atoms. Examples of such divalent groups include alkylene of about 2 to 12 carbon atoms, cyclohexylene and arylene. Specific examples of the alkylene and cycloalkylene groups include ethylene, trimethylene, 1,3-butanediyl, 2,2-dimethyl-1,3-propanediyl, 1,1,2-triphenylethanediyl, 2,2,4-trimethyl-1,3-pentanediyl, 1,2-cyclohexylene, and the like. Examples of the arylene groups which $R^1$ and $R^2$ collectively may represent are given herein below as formulas (V), (VI) and (VII).

The divalent groups that $R^1$ and $R^2$ collectively may represent include radicals having the formula

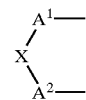

wherein
each of $A^1$ and $A^2$ is an arylene radical, e.g., a divalent, carbocyclic aromatic group containing 6 to 10 ring carbon atoms, wherein each ester oxygen atom of fluorophosphite (I) is bonded to a ring carbon atom of $A^1$ and $A^2$.

X is (i) a chemical bond directly between ring carbon atoms of $A^1$ and $A^2$;
or (ii) an oxygen atom, a group having the formula —(CH$_2$)$_y$— wherein y is 2 to 4 or a group having the formula

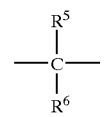

wherein $R^5$ is hydrogen, alkyl or aryl, e.g., the aryl groups illustrated by formulas (II), (III) and (IV), and $R^6$ is hydrogen or alkyl. The total carbon content of the group —C($R^5$)($R^6$)— normally will not exceed 20 and, preferably, is in the range of 1 to 8 carbon atoms. Normally, when $R^1$ and $R^2$ collectively represent a divalent hydrocarbylene group, the phosphite ester oxygen atoms, i.e. the oxygen atoms depicted in formula (I), are separated by a chain of atoms containing at least 3 carbon atoms.

Examples of the arylene groups represented by each of $A^1$ and $A^2$ include the divalent radicals having the formulas:

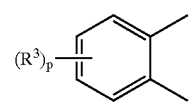

(V)

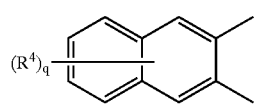

(VI)

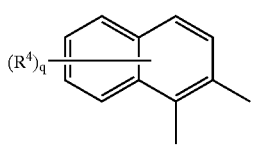

(VII)

wherein $R^3$ and $R^4$ may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts and the like. The alkyl moiety of such alkyl, alkoxy, alkanoyl, alkoxycarbonyl and alkanoyloxy groups typically contains up to about 8 carbon atoms. Although it is possible for p to represent 0 to 4 and for q to represent 0 to 6, the value of each of p and q usually will not exceed 2. $R^3$ and $R^4$ preferably represent lower alkyl groups, i.e., straight-chain and branched-chain alkyl of up to about 4 carbon atoms, and p and q each represent 0, 1 or 2.

The fluorophosphite esters that are most preferred, e.g., those which exhibit the best stability, are those wherein the fluorophosphite ester oxygen atoms are bonded directly to a ring carbon atom of a carbocyclic, aromatic group, e.g., an aryl or arylene group represented by any of formulas (II) through (VII). When $R^1$ and $R^2$ individually each represents an aryl radical, e.g., a phenyl group, it is further preferred that 1 or both of the ring carbon atoms that are in a position ortho to the ring carbon atoms bonded to the fluorophosphite ester oxygen atom are substituted with an alkyl group, especially a branched chain alkyl group such as isopropyl, tert-butyl, tert-octyl and the like. Similarly, when $R^1$ and $R^2$ collectively represent a radical having the formula

the ring carbon atoms of arylene radicals $A^1$ and $A^2$ that are in a position ortho to the ring carbon atoms bonded to the fluorophosphite ester oxygen atom are substituted with an alkyl group, preferably a branched chain alkyl group such as isopropyl, tert-butyl, tert-octyl and the like.

The most preferred fluorophosphite esters have the general formula

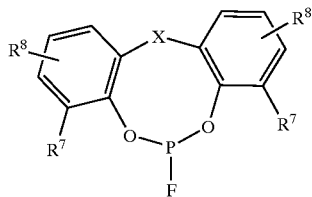

wherein each $R^7$ is alkyl of 3 to 8 carbon atoms; each $R^8$ is hydrogen, alkyl of 1 to 8 carbon atoms or alkoxy of 1 to 8 carbon atoms; and X is (i) a chemical bond directly between ring carbon atoms of each phenylene group to which X is bonded; or (ii) a group having the formula

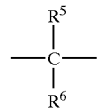

wherein each of $R^5$ and $R^6$ is hydrogen or alkyl of 1 to 8 carbon atoms.

The fluorophosphite esters of formula (I) may be prepared by published procedures or by techniques analogous thereto. See, for example, the procedures described by Riesel et al., J. Z. Anorg. Allg. Chem., 603, 145 (1991), Tullock et al., J. Org. Chem., 25, 2016 (1960), White et al., J. Am. Chem. Soc., 92, 7125 (1970) and Meyer et al., Z. Naturforsch, Bi. Chem. Sci., 48, 659 (1993) and in U.S. Pat. No. 4,912,155. The organic moiety of the fluorophosphite compounds, i.e., the residue(s) represented by $R^1$ and $R^2$ can be derived from chiral or optically active compounds. Fluorophosphite ligands derived from chiral glycols or phenols will generate chiral ligands.

The catalyst systems comprise a combination of one or more transition metals selected from the Group VIII metals and rhenium and one or more of the fluorophosphite compounds described in detail hereinabove. The transition metal may be provided in the form of various metal compounds such as carboxylate salts of the transition metal. Rhodium compounds that may be used as a source of rhodium for the active catalyst include rhodium II or rhodium III salts of carboxylic acids, examples of which include di-rhodium tetraacetate dihydrate, rhodium(II) acetate, rhodium(II) isobutyrate, rhodium(II) 2-ethylhexanoate, rhodium(II) benzoate and rhodium(II) octanoate. Also, rhodium carbonyl species such as $Rh_4(CO)_{12}$, $Rh_6(CO)_{16}$ and rhodium(I) acetylacetonate dicarbonyl may be suitable rhodium feeds. Additionally, rhodium organophosphine complexes such as tris(triphenylphosphine) rhodium carbonyl hydride may be used when the phosphine moieties of the complex fed are easily displaced by the fluorophosphite ligands of the present invention. Less desirable rhodium sources are rhodium salts of strong mineral acids such as chlorides, bromides, nitrates, sulfates, phosphates and the like.

The ratio of gram moles fluorophosphite ligand to gram atoms transition metal can vary over a wide range, e.g., gram mole fluorophosphite:gram atom transition metal ratios of about 1:1 to 200:1. For the rhodium-containing catalyst systems the gram mole fluorophosphite:gram atom rhodium ratio preferably is in the range of about 1:1 up to 70:1 with ratios in the range of about 1:1 to 50:1 being particularly preferred.

The fluoride reducing additive may be any material that will reduce the amount of fluoride present in a process, while not adversely effect the activity of a fluorophosphite-containing transition metal catalyst. The additive may be used in any amount that is sufficient to reduce the level of fluoride content to any desired extent. Moreover, the additive may be introduced into the reaction mixture of the process in any manner. Examples of materials suitable for use as fluoride reducing reaction mixture additives are oxides, carboxylates, hydroxides, bicarbonates, carbonates, phosphates, citrates, borates and/or ascorbates of calcium, sodium, magnesium, aluminum, zinc, silver, lithium, potassium, copper, cadmium, barium, and/or silicon. Examples of carboxylates are those obtained from carboxylic acids containing 1–20 carbon atoms, such as formic, propionic, hexanoic, heptanoic, octanoic, decanoic, dodecanoic, tetradecanoic, hexadecanoic, stearic or eicosanic acids. Also suitable for use as additives are mixed salts such as magnesium aluminum carbonates (also known as talcites and hydrotalcites); molecular sieves; ion exchange resins; membranes, and the like. More preferably, the fluoride reducing additive is a calcium salt such as calcium stearate or calcium acetate, or a magnesium salt such as magnesium stearate, or the like. Mixtures of the additives may also be used in the process.

The invention will be more readily understood by reference to the following examples. There are, of course, many other forms of this invention which will become obvious to one skilled in the art, once the invention has been fully disclosed, and it will accordingly be recognized that these examples are given for the purpose of illustration only, and are not to be construed as limiting the scope of this invention in any way.

EXAMPLES

In the following examples, fluoride concentrations were determined as follows.

Method for Analyzing Fluoride Concentrations

The method described below is a modification of the measurement method described in the manual for the Orion Fluoride Combination Electrode model #96-09. The method uses a buffer referred to as TISAB II. TISAB stands for Total Ionic Strength Adjuster Buffer and it is used to provide constant background ionic strength, decomplex fluoride, and adjust solution pH.

The concentration of hydrofluoric acid contained in a sample was determined by shaking the sample with an equal amount of TISAB II buffer (Orion #940909, recommended buffer for use with a fluoride selective electrode) and separating out the buffer portion. An equal amount of distilled water is added to the buffer portion and the fluoride concentration is measured with an Orion (#96-09) fluoride ion selective electrode that is attached to a Metrohm 751 GPD Titrino titrator. The measurement is in millivolts and this is converted into parts per million (ppm) by using a calibration chart.

In the following examples, a fluorophosphite-containing transition metal catalyst is used to hydroformylate propylene into butyraldehydes. The hydroformylation process is operated with, or in the absence of, a reaction mixture additive to reduce fluoride content. The hydroformylation process is carried out in a vapor take-off reactor consisting of a vertically arranged stainless steel pipe having a 2.5 centimeter inside diameter and a length of 1.2 meters. The reactor has a filter element welded into the side near the bottom of the reactor for the inlet of gaseous reactants. The reactor contains a thermowell which is arranged axially with the reactor in its center for measurement of the temperature of the hydroformylation reaction mixture. The bottom of the reactor has a high pressure tubing connection that is connected to a cross. One of the connections to the cross permits the addition of non-gaseous reactants such as octene-1 or make-up solvent, another leads to the high-pressure connection of a differential pressure (D/P) cell that is used to measure catalyst level in the reactor and the bottom connection is used for draining the catalyst solution at the end of the run.

In the hydroformylation of propylene in a vapor take-off mode of operation, the hydroformylation reaction mixture or solution containing the catalyst is sparged under pressure with the incoming reactants of propylene, hydrogen and carbon monoxide as well as any inert feed such as nitrogen. As butyraldehyde is formed in the catalyst solution, the butyraldehyde and unreacted reactant gases are removed as a vapor from the top of the reactor by a side-port. The vapor removed is chilled in a high pressure separator where the butyraldehyde product is condensed along with some of the unreacted propylene. The uncondensed gases are let down to atmospheric pressure via the pressure control valve. These gases pass through a series of dry-ice traps where any other aldehyde product is collected. The product from the high pressure separator is combined with that of the traps, and is subsequently weighed and analyzed by standard gas/liquid phase chromatography (GLC) techniques for the net weight and normal/iso ratio of the butyraldehyde product.

The gaseous feeds to the reactor are fed to the reactor via twin cylinder manifolds and high pressure regulators. The hydrogen passes through a commercially available Deoxo® (registered trademark of Engelhard Inc.) catalyst bed to remove any oxygen contamination and through a flow controller D/P cell and control valve. The carbon monoxide passes through a similar Deoxo® bed heated to 125 C, and iron carbonyl removal bed (as disclosed in U.S. Pat. No. 4,608,239). Nitrogen can be added to the feed mixture as an inert gas. Nitrogen, when added, is metered and then mixed with the hydrogen feed prior to the hydrogen Deoxo® bed. Propylene is fed to the reactor from feed tanks that are pressurized with hydrogen. The propylene feed rate is controlled by a liquid mass flow meter. The rate of level drop in the tank is also measured in conjunction with the meter. All gases and propylene are passed through a preheater to insure vaporization of the liquid propylene.

Example 1

(Comparative)

A catalyst solution was prepared under nitrogen using a charge of 0.0375 g rhodium dicarbonyl acetonylacetate, (also known as rhodium dicarbonyl acac, 15 mg Rh), 2.12 g 2,2'-ethylidene bis(4,6-di-t-butyl-phenyl)fluorophosphite, (4.37 mmoles, [L]/[Rh]=30), and 190 ml of dioctylphthalate. This was charged to the reactor under an argon blanket and the reactor sealed. The reactor was pressured to 260 psig (18.9 Bar) with hydrogen, carbon monoxide and nitrogen and heated to 145° C. Propylene feed was then started and the flows were adjusted to the following reported as liters/min at standard temperature and pressure (STP): hydrogen= 3.70 l/min STP; carbon monoxide=3.70 l/min STP; nitrogen=1.12 l/min STP and propylene=2.08 l/min STP. This is equivalent to having the following partial pressures in the feed to the reactor reported as psia: hydrogen=96 (6.6 Bar); carbon monoxide=96 (6.6 Bar); nitrogen=29 (2.0 Bar); and propylene=54 psia (3.7 Bar).

The reaction was carried out under the above conditions for five hours. The butyraldehyde production rate for the last three hours of operation averaged 68.0 g/hour for a catalyst activity of 4.45 kilograms butyraldehyde/gram of rhodium-hour. The product n:iso ratio was 2.05/1.

The fluoride concentration in the aldehyde product was determined hourly during the reaction. The amount of fluoride measured in the aldehyde each hour was 0.26 ppm, 0.8 ppm, 1.7 ppm, 1.8 ppm, and 2.1 ppm respectively.

Example 2

A catalyst solution was prepared under nitrogen using a charge of 0.0375 g rhodium dicarbonyl acetonylacetate, (15 mg Rh), 2.12 g 2,2'-ethylidene bis(4,6-di-t-butyl-phenyl) fluorophosphite, (4.37 mmoles, [L]/[Rh]=30), 0.06 g of calcium stearate as a fluoride reducing additive and 190 ml of dioctylphthalate. This was charged to the reactor under an argon blanket and the reactor sealed. The reactor was pressured to 260 psig (18.9 Bar) with hydrogen, carbon monoxide and nitrogen and heated to 145° C. Propylene feed was then started and the flows were adjusted to the following reported as liters/min at standard temperature and pressure (STP); hydrogen=3.70 l/min STP; carbon monoxide=3.70 l/min STP; nitrogen=1.12 l/min STP and propylene=2.08 l/min STP. This is equivalent to having the following partial pressures in the feed to the reactor reported as psia; hydrogen=96 (6.6 Bar); carbon monoxide=96 (6.6 Bar); nitrogen=29 (2.0 Bar); and propylene=54 psia (3.7 Bar).

The reaction was carried out under the above conditions for five hours. The butyraldehyde production rate for the last three hours of operation averaged 60.8 g/hour for a catalyst activity of 3.92 kilograms butyraldehyde/gram of rhodium-hour. The product n:iso ratio was 2.02/1.

The fluoride concentration in the aldehyde product was determined hourly during the reaction. The amount of fluoride measured in the aldehyde each hour was 0.26 ppm, 0.11 ppm, 0.08 ppm, 0.075 ppm and 0.045 ppm respectively.

Example 3

(Comparative)

A catalyst solution was prepared under nitrogen using a charge of 0.0375 g rhodium dicarbonyl acetonylacetate, (15 mg Rh), 1.06 g 2,2'-ethylidene bis(4,6-di-t-butyl-phenyl) fluorophosphite, (2.18 mmoles, [L]/[Rh]=15), and 190 ml of dioctylphthalate. The catalyst solution was charged to the reactor under an argon blanket and the reactor was sealed. The reactor was pressured to 260 psig (18.9 Bar) with hydrogen, carbon monoxide and nitrogen and heated to 115° C. Propylene feed was then started and the flows were adjusted to the following reported as liters/min at standard temperature and pressure (STP): hydrogen=3.70 l/min STP; carbon monoxide=3.70 l/min STP; nitrogen=1.12 l/min STP and propylene=2.08 l/min STP. This is equivalent to having the following partial pressures in the feed to the reactor reported as psia: hydrogen=96 (6.6 Bar); carbon monoxide=96 (6.6 Bar); nitrogen=29 (2.0 Bar); and propylene=54 psia (3.7 Bar).

The reaction was carried out under the above conditions for five hours. The butyraldehyde production rate for the last three hours of operation averaged 98.13 g/hour for a catalyst activity of 6.45 kilograms butyraldehyde/gram of rhodium-hour. The product n:iso ratio was 2.68/1.

The fluoride concentration in the aldehyde product was determined hourly during the reaction. The amount of fluoride measured in the aldehyde each hour was 1.7 ppm, 0.16 ppm, 0.49 ppm, 0.18 ppm, and 0.19 ppm respectively.

Example 4

A catalyst solution was prepared under nitrogen using a charge of 0.0375 g rhodium dicarbonyl acetonylacetate, (15 mg Rh), 1.06 g 2,2'-ethylidene bis(4,6-di-t-butyl-phenyl) fluorophosphite, (2.18 mmoles, [L]/[Rh]=15), 0.06 g of calcium acetate as a fluoride reducing additive and 190 ml of dioctylphthalate. The catalyst solution was charged to the reactor under an argon blanket and the reactor was sealed. The reactor was pressured to 260 psig (18.9 Bar) with hydrogen, carbon monoxide and nitrogen and heated to 115° C. Propylene feed was then started and the flows were adjusted to the following reported as liters/min at standard temperature and pressure (STP): hydrogen=3.70 l/min STP; carbon monoxide=3.70 l/min STP; nitrogen=1.12 l/min STP and propylene=2.08 l/min STP. This is equivalent to having the following partial pressures in the feed to the reactor reported as psia: hydrogen=96 (6.6 Bar); carbon monoxide=96 (6.6 Bar); nitrogen=29 (2.0 Bar); and propylene=54 psia (3.7 Bar).

The reaction was carried out under the above conditions for five hours. The butyraldehyde production rate for the last three hours of operation averaged 83.7 g/hour for a catalyst activity of 5.33 kilograms butyraldehyde/gram of rhodium-hour. The product n:iso ratio was 2.58/1.

The fluoride concentration in the aldehyde product was determined hourly during the reaction. The amount of fluoride measured in the aldehyde each hour was 0.12 ppm, 0.035 ppm, 0.025 ppm, 0.024 ppm, and 0.018 ppm respectively.

Example 5

A catalyst solution was prepared under nitrogen using a charge of 0.0375 g rhodium dicarbonyl acetonylacetate, (15 mg Rh), 1.06 g 2,2'-ethylidene bis(4,6-di-t-butyl-phenyl) fluorophosphite, (2.18 mmoles, [L]/[Rh]=15), 0.06 g of calcium stearate as a fluoride reducing additive and 190 ml of dioctylphthalate. The catalyst solution was charged to the reactor under an argon blanket and the reactor was sealed. The reactor was pressured to 260 psig (18.9 Bar) with hydrogen, carbon monoxide and nitrogen and heated to 115° C. Propylene feed was then started and the flows were adjusted to the following reported as liters/min at standard temperature and pressure (STP): hydrogen=3.70 l/min STP; carbon monoxide=3.70 l/min STP; nitrogen=1.12 l/min STP and propylene=2.08 l/min STP. This is equivalent to having the following partial pressures in the feed to the reactor reported as psia: hydrogen=96 (6.6 Bar); carbon monoxide=96 (6.6 Bar); nitrogen=29 (2.0 Bar); and propylene=54 psia (3.7 Bar).

The reaction was carried out under the above conditions for five hours. The butyraldehyde production rate for the last three hours of operation averaged 99.5 g/hour for a catalyst activity of 6.36 kilograms butyraldehyde/gram of rhodium-hour. The product n:iso ratio was 2.59/1.

The fluoride concentration in the aldehyde product was determined hourly during the reaction. The amount of fluoride measured in the aldehyde each hour was 0.014 ppm, 0.012 ppm, 0.004 ppm, 0.0018 ppm, and 0.006 ppm.

Example 6

A catalyst solution was prepared under nitrogen using a charge of 0.0375 g rhodium dicarbonyl acetonylacetate, (15 mg Rh), 1.06 g 2,2'-ethylidene bis(4,6-di-t-butyl-phenyl) fluorophosphite, (2.18 mmoles, [L]/[Rh]=15), 0.06 g of magnesium stearate as a fluoride reducing additive and 190 ml of dioctylphthalate. The catalyst solution was charged to the bench unit reactor under an argon blanket and the reactor was sealed. The reactor was pressured to 260 psig (18.9 Bar) with hydrogen, carbon monoxide and nitrogen and heated to 115° C. Propylene feed was then started and the flows were adjusted to the following reported as liters/min at standard temperature and pressure (STP): hydrogen=3.70 l/min STP; carbon monoxide=3.70 l/min STP; nitrogen=1.12 l/min STP and propylene=2.08 l/min STP. This is equivalent to having the following partial pressures in the feed to the reactor reported as psia: hydrogen=96 (6.6 Bar); carbon monoxide=96 (6.6 Bar); nitrogen=29 (2.0 Bar); and propylene=54 psia (3.7 Bar).

The reaction was carried out under the above conditions for five hours. The butyraldehyde production rate for the last three hours of operation averaged 83.4 g/hour for a catalyst activity of 5.36 kilograms butyraldehyde/gram of rhodium-hour. The product n:iso ratio was 2.52/1.

The fluoride concentration in the aldehyde product was determined hourly during the reaction. The amount of fluoride measured in the aldehyde each hour was 0.013 ppm, 0.013 ppm, 0.012 ppm, 0.0012 ppm, and 0.01 ppm respectively.

The examples demonstrate that the present invention successfully reduced the fluoride content of a process wherein a fluorophosphite-containing transition metal catalyst was utilized.

While this invention has been described with respect to particular embodiments thereof, it is apparent that numerous other modifications of the invention will be obvious to those skilled in the art. The appended claims and this invention generally should be construed to cover all such obvious forms and modifications which are in the true spirit and scope of the present invention.

We claim:

1. A method for reducing the fluoride content in a chemical process, wherein said chemical process is selected from the group consisting of hydroformylation, hydrogenation, isomerization, hydrocyanation, hydrosilation, cyclopropanation, telomerizations, carbon hydrogen bond activation, olefin metathesis, olefin copolymerizations, butadiene dimerization, oligomerization, butadiene polymerization, the Heck reaction and arene coupling reaction, wherein said chemical process comprises reacting a reactant mixture in the presence of a catalyst comprising one or more transition metals selected from the group consisting of Group VIII metals and rhenium, and one or more fluorophosphite compounds having the general formula

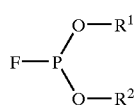
(1)

wherein $R^1$ and $R^2$ are hydrocarbyl radicals which contain a total of up to about 40 carbon atoms and wherein the ratio of gram moles fluorophosphite ligand to gram atoms transition metal is at least 1:1, to produce a product containing fluoride, said method comprising introducing an additive into said reactant mixture, in an amount sufficient for the purpose of reducing the fluoride concentration in said product, wherein said additive is selected from the group consisting of (a) oxides, carboxylates, hydroxides, bicarbonates, carbonates, phosphates, citrates, borates and ascorbates, of calcium, sodium, magnesium, aluminum, zinc, silver, lithium, potassium, copper, cadmium, barium, and silicon, and mixtures thereof, and (b) talcites, hydrotalcites, molecular sieves, ion exchange resins, membranes, and mixtures thereof.

2. The process according to claim 1 wherein said chemical process is a hydroformylation of an olefin to produce an aldehyde.

3. The process according to claim 1 wherein said additive is selected from the group consisting of carboxylates of calcium, sodium, magnesium, aluminum, zinc, silver, lithium, potassium, copper, cadmium, barium, and silicon containing 1–20 carbon atoms, and mixtures thereof.

4. The process according to claim 1 wherein said additive is selected from the group consisting of talcites, hydrotalcites, molecular sieves, ion exchange resins, membranes, and mixtures thereof.

5. The process according to claim 1 wherein said additive is selected from the group consisting of a calcium salt, a magnesium salt, and mixtures thereof.

6. The process according to claim 1 wherein said additive is selected from the group consisting of a calcium carboxylate, a magnesium carboxylate, and mixtures thereof.

7. The process according to claim 1 wherein said additive is selected from the group consisting of calcium stearate, calcium acetate, magnesium stearate, and mixtures thereof.

8. The process according to claim 1 wherein said additive is calcium stearate.

9. A method for reducing the fluoride content in a hydroformylation process, wherein said process comprises reacting an alkenyl olefin in a reactant mixture in the presence of a catalyst comprising one or more transition metals selected from the group consisting of Group VIII metals and rhenium, and one or more fluorophosphite compounds having the general formula

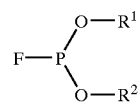
(1)

wherein $R^1$ and $R^2$ are hydrocarbyl radicals which contain a total of up to about 40 carbon atoms and wherein the ratio of gram moles fluorophosphite ligand to gram atoms transition metal is at least 1:1, to produce an aldehyde product containing fluoride, said method comprising introducing an additive into said reactant mixture in an amount sufficient for the purpose of reducing the fluoride concentration in said aldehyde product, wherein said additive is selected from the group consisting of (a) oxides, carboxylates, hydroxides, bicarbonates, carbonates, phosphates, citrates, borates and ascorbates, of calcium, sodium, magnesium, aluminum, zinc, silver, lithium, potassium, copper, cadmium, barium, and silicon, and mixtures thereof, and (b) talcites, hydrotalcites, molecular sieves, ion exchange resins, membranes, and mixtures thereof.

10. The process according to claim 9 wherein said additive is selected from the group consisting of carboxylates of calcium, sodium, magnesium, aluminum, zinc, silver, lithium, potassium, copper, cadmium, barium, and silicon containing 1–20 carbon atoms, and mixtures thereof.

11. The process according to claim 9 wherein said additive is selected from the group consisting of talcites, hydrotalcites, molecular sieves, ion exchange resins, membranes, and mixtures thereof.

12. The process according to claim 9 wherein said additive is selected from the group consisting of a calcium salt, a magnesium salt, and mixtures thereof.

13. The process according to claim 9 wherein said additive is selected from the group consisting of a calcium carboxylate, a magnesium carboxylate, and mixtures thereof.

14. The process according to claim 9 wherein said additive is selected from the group consisting of calcium stearate, calcium acetate, magnesium stearate, and mixtures thereof.

15. The process according to claim 9 wherein said additive is calcium stearate.

16. The process according to claim 9 wherein said aldehyde product is a mixture of isobutyraldehyde and normal butyraldehyde.

* * * * *